United States Patent
DeSisto et al.

[19]

[11] Patent Number: 5,951,548
[45] Date of Patent: Sep. 14, 1999

[54] SELF-EVACUATING ELECTROCAUTERY DEVICE

[75] Inventors: Stephen R. DeSisto, 2525 Arapahoe Ave. Suite E4-243, Boulder, Colo. 80302; Robert G. Walter, Lafayette, Colo.

[73] Assignee: Stephen R. DeSisto, Boulder, Colo.

[21] Appl. No.: 08/804,055

[22] Filed: Feb. 21, 1997

[51] Int. Cl.$^6$ .................................................. A61B 17/39
[52] U.S. Cl. ............................... 606/42; 606/45; 606/49; 604/35
[58] Field of Search .................................. 606/42, 45, 49; 604/35

[56] References Cited

U.S. PATENT DOCUMENTS

| | | |
|---|---|---|
| 2,808,833 | 10/1957 | August . |
| 2,888,928 | 6/1959 | Seiger . |
| 3,651,293 | 3/1972 | Hoffman . |
| 3,801,766 | 4/1974 | Morrison et al. . |
| 3,825,004 | 7/1974 | Durden, III . |
| 3,828,780 | 8/1974 | Morrison, Jr. . |
| 3,902,494 | 9/1975 | Haberlen et al. . |
| 3,906,955 | 9/1975 | Roberts . |
| 3,974,833 | 8/1976 | Durden, III . |
| 4,095,071 | 6/1978 | Chamberlain . |
| 4,347,842 | 9/1982 | Beale . |
| 4,394,553 | 7/1983 | Feil . |
| 4,445,517 | 5/1984 | Feild . |
| 4,450,325 | 5/1984 | Luque . |
| 4,465,908 | 8/1984 | Griffith et al. . |
| 4,654,488 | 3/1987 | Westfall . |
| 4,686,981 | 8/1987 | Forintos . |
| 4,695,692 | 9/1987 | Noda . |
| 4,719,914 | 1/1988 | Johnson . |
| 4,904,833 | 2/1990 | Sato et al. . |
| 4,924,047 | 5/1990 | Tsuge . |
| 5,026,370 | 6/1991 | Lottick ........................................ 606/42 |
| 5,055,100 | 10/1991 | Olsen . |
| 5,133,714 | 7/1992 | Beane . |
| 5,181,916 | 1/1993 | Reynolds et al. . |
| 5,192,267 | 3/1993 | Shapira et al. . |
| 5,195,959 | 3/1993 | Smith . |

(List continued on next page.)

OTHER PUBLICATIONS

Gatti, John E., et al, *The Mutagenicity of Electrocautery Smoke*, Plastic and Reconstructive Surgery, May 1992, pp. 781–784.

Gatti, John E., et al, *The Mutagenicity of Electrocautery Smoke*, Discussion by William R. Kanter, M.D., Plastic and Reconstructive Surgery, May 1992, pp. 785–786.

*Primary Examiner*—Lee Cohen
*Attorney, Agent, or Firm*—Emery L. Tracy

[57] ABSTRACT

An electrosurgical instrument for selectively providing electrical energy from an electrosurgical generator to an electrode blade for searing and coagulation is provided. The instrument comprises a hollow body having a first and second hollow area and a cable connected to the generator having a main contact wire and first and second switch wires with a main conducting strip connected electrically to the blade. First and second switch conducting strips are selectively connected to the main conducting strip. A receiver receives the blade and is electrically connected to the main contact wire to provide electrical connection between the contact wire and the blade. The blade extends from the first hollow portion with at least one plume intake port formed in the body receiving the surgery associated plume into the first hollow portion. A switch mechanism positioned between the first and second hollow portions selectively connects one of the first and second switch conducting strips to the main conducting strip such that a selected electrical energy is transmitted to the blade. An airway path assembly within the switch mechanism connects the first hollow portion to the second hollow portion when the switch mechanism selectively connects one of the first and second switch conducting strips to the main conducting strip. A vacuum mechanism is connected to the second hollow portion to evacuate the plume from the second hollow portion with the vacuum mechanism being activated upon the switch selectively connecting either the first or second switch conducting strip to the main conducting strip.

14 Claims, 4 Drawing Sheets

U.S. PATENT DOCUMENTS

| | | |
|---|---|---|
| 5,213,204 | 5/1993 | Sommer . |
| 5,224,944 | 7/1993 | Elliott . |
| 5,242,442 | 9/1993 | Hirschfeld . |
| 5,244,462 | 9/1993 | Delahuerga et al. . |
| 5,260,534 | 11/1993 | Chung . |
| 5,269,781 | 12/1993 | Hewell, III . |
| 5,318,565 | 6/1994 | Kuriloff et al. . |
| 5,342,349 | 8/1994 | Kaufman . |
| 5,360,427 | 11/1994 | Majlessi . |
| 5,368,560 | 11/1994 | Rambo et al. . |
| 5,376,089 | 12/1994 | Smith . |
| 5,800,431 | 9/1998 | Brown ................................ 606/42 |

SELF-EVACUATING ELECTROCAUTERY DEVICE

BACKGROUND OF THE INVENTION

1. Field of the Invention

This invention relates generally to electrosurgical instruments for selectively providing electrical energy from an electrosurgical generator to a patient for searing and coagulating tissue and the like and, more particularly, it relates to electrosurgical instruments for selectively providing electrical energy from an electrosurgical generator to a patient for searing and coagulating tissue and the like which further provides evacuation of the plume associated with the searing and coagulating of the tissue and the like.

2. Description of the Prior Art

With known prior art electrocautery devices, a plume, as it is referred to by persons skilled in the art, is created during surgery by the vaporization of organic material (i.e., the tissue of the patient) which has been ablated by the electric current of the electrocautery device. It is widely known in the medical field that the plume created during electrosurgery is offensive and potentially dangerous to the surgeons and other operating room staff The high temperature plume, which rises rapidly from the point of the electrosurgical instrument, has been shown to contain possible carcinogenic elements. In fact, of particular significance and concern, it has been discovered that the plume produced by electrosurgical incisions and cauterizations potentially contain and transport viable viral DNA. The viruses transmitted by the plume present a significant health hazard to the operating surgeon and others present in the operating room. In addition to the health hazards to operating personnel, sometimes the plume is produced in such volume that the surgeon's view of the operative field is obscured thereby placing the patient at substantial risk.

In the prior art, systems have been developed for aspirating the plume produced by electrocautery devices in electrosurgical procedures. In the typical technique, the plume is aspirated by a conventional hospital suction tube held near the site of electrosurgical procedure by an assistant. Unfortunately, this method inefficiently requires the full-time attention of the assistant and the placement of the often bulky suction tube in the operative field obstructs the operating surgeon's view. Additionally, since conventional suction tubes create substantial noise levels in the operating room coupled with the fact that the suction tubes operate on a continuous basis during surgery, the suction tubes interfere with normal operating room dialogue thereby potentially causing miscommunications and misunderstandings between the operating room surgeon and the operating room staff.

Systems have been developed in an attempt to overcome the disadvantages described above. In particular, the August, U.S. Pat. No. 2,808,833, the Seiger, U.S. Pat. No. 2,888,928, and the Forintos, U.S. Pat. No. 4,686,981, describe surgical instruments having suction devices attached thereto. Specifically, the August patent and the Forintos patent describe suction devices for the express purpose of withdrawing excess blood or bodily fluids prior to coagulating the remaining vessels. The Seiger patent describes a coagulating surgical instrument which includes a plurality of suction openings disposed at right angles with respect to the longitudinal axis of the cautery tip. The suction of the Seiger patent's surgical instrument operates in an area which is not immediately adjacent to the coagulating area, thus, not effectively producing the desired plume evacuation result. Furthermore, since the suction of the Seiger patent is operating continually, the noise of the suction device further impedes communication among the surgical team.

There are other known plume and tissue removal systems integrated with electrosurgical instruments, such as described in the Olsen, U.S. Pat. No. 5,055,100 and the Johnson, U.S. Pat. No. 4,719,914. Although the Olsen patent and the Johnson patent describe electrocautery devices having a suction passage adjacent the cutting end of the electrocautery device, the particular construction of each of these devices result in increased difficulty for the surgeons during operations. In particular, the devices are limited by their structure to removing only the plume which is immediately adjacent the inlet of the suction tube opening. Also, the construction of the devices render the vacuum suction tube closely adjacent the tip of the blade which actually generates the plume. Thus, the plume or the suction tube itself obscures the surgical field from the view of the surgeon. Furthermore, in the Olsen patent and the Johnson patent, it is not possible to effectively remove the plume since the suction tubes are intended for primarily removing bodily fluids and tend to clog with the removed bodily fluids. Therefore, due to the ineffectiveness of the Olsen patent and the Johnson patent in failing to remove the plume, the importance of effectively removing the plume created by the electrocautery device from the surgical fields remains.

It is an object of the present invention to provide a self-evacuating electrocautery device which effectively removes the plume created during surgical operations to minimize health hazards to the operating surgeons and the other operating staff.

It is another object of the present invention to provide a self-evacuating electrocautery device which effectively removes the plume created during surgical operations and which does not unduly interfere with the operating surgeon's field of view.

It is yet a further object of the present invention to provide a self-evacuating electrocautery device which effectively removes the plume created during surgical operations and which activates a vacuum to remove the plume only during activation of the electrocautery device.

It is still a further object of the present invention to provide a self-evacuating electrocautery device which effectively removes the plume created during surgical operations and which does not interfere with the operating surgeons use of the electrocautery device as an electrosurgical instrument.

SUMMARY OF THE INVENTION

The present invention is an electrocautery device for selectively providing electrical energy from an electrosurgical generator for alternatively searing and coagulating tissue and the like of a patient during surgery. The electrocautery device has a blade and a cable electrically connecting the blade to the electrosurgical generator.

The electrocautery device of the present invention comprises a main body and vacuum means associated with the main body for selectively providing a vacuum for removing any plume created while searing or coagulating tissue with the blade of the electrosurgical instrument. The device further comprises switch means secured to the main body for selectively controlling the electrical energy to the blade. The switch means selectively activate the vacuum means only upon activation of the electrical energy.

In an embodiment of the present invention, the device comprises an electrical contact within the main body with the electrical contact electrically connecting the blade and the electric cable to selectively control the electrical charge to the blade to either sear or coagulate tissue and to activate the vacuum means. The electrical contact further comprises means for releasably securing the blade to the electrical contact.

In another preferred embodiment, the electrocautery device of the present invention comprises the main body having an elongated hollow body including a longitudinal length, a first opening and a second opening. The first opening receives the blade and the second opening receives the electrical cable. Furthermore, the hollow body comprises a first body portion and a second body portion with the first body portion being secured to the second body portion by ultrasonic welding.

In yet another preferred embodiment, the electrocautery device of the present invention comprises the first and second body portions having a plurality of ribs adjacent the first and second openings of the hollow body to inhibit movement of the blade and electrical cable, respectively, within the hollow body. Additionally, the first and second body portions include stabilizing supports about the switch means to inhibit movement of the switch means along the longitudinal length of the hollow body.

In still another preferred embodiment, the electrocautery device of the present invention comprises the vacuum means comprising at least one intake port formed adjacent the first opening of the hollow body, a vacuum tubing extending through the second opening of the hollow body and connected to the intake ports, a vacuum source for creating a vacuum, and a waste receptacle connected to the vacuum tubing for receiving the plume. Furthermore, preferably, the electrocautery device of the present invention comprises the switch means comprising a self-centering switch body rotatable within the hollow body to selectively activate the electrical energy of the electrosurgical generator to either sear or coagulate tissue and to activate the vacuum means upon activation of the electrical energy. The switch means further comprise path means formed in the switch body for selectively connecting the intake ports to the vacuum tubing upon activation of both the electrical energy to either sear or coagulate tissue and the vacuum means. Preferably, the path means comprise a pair of intersecting airway paths alternatively alignable within the hollow body to connect the intake ports to the vacuum tubing upon activation of both the electrical energy and the vacuum means.

DETAILED DESCRIPTION OF THE PREFERRED EMBODIMENTS

Figure 1:
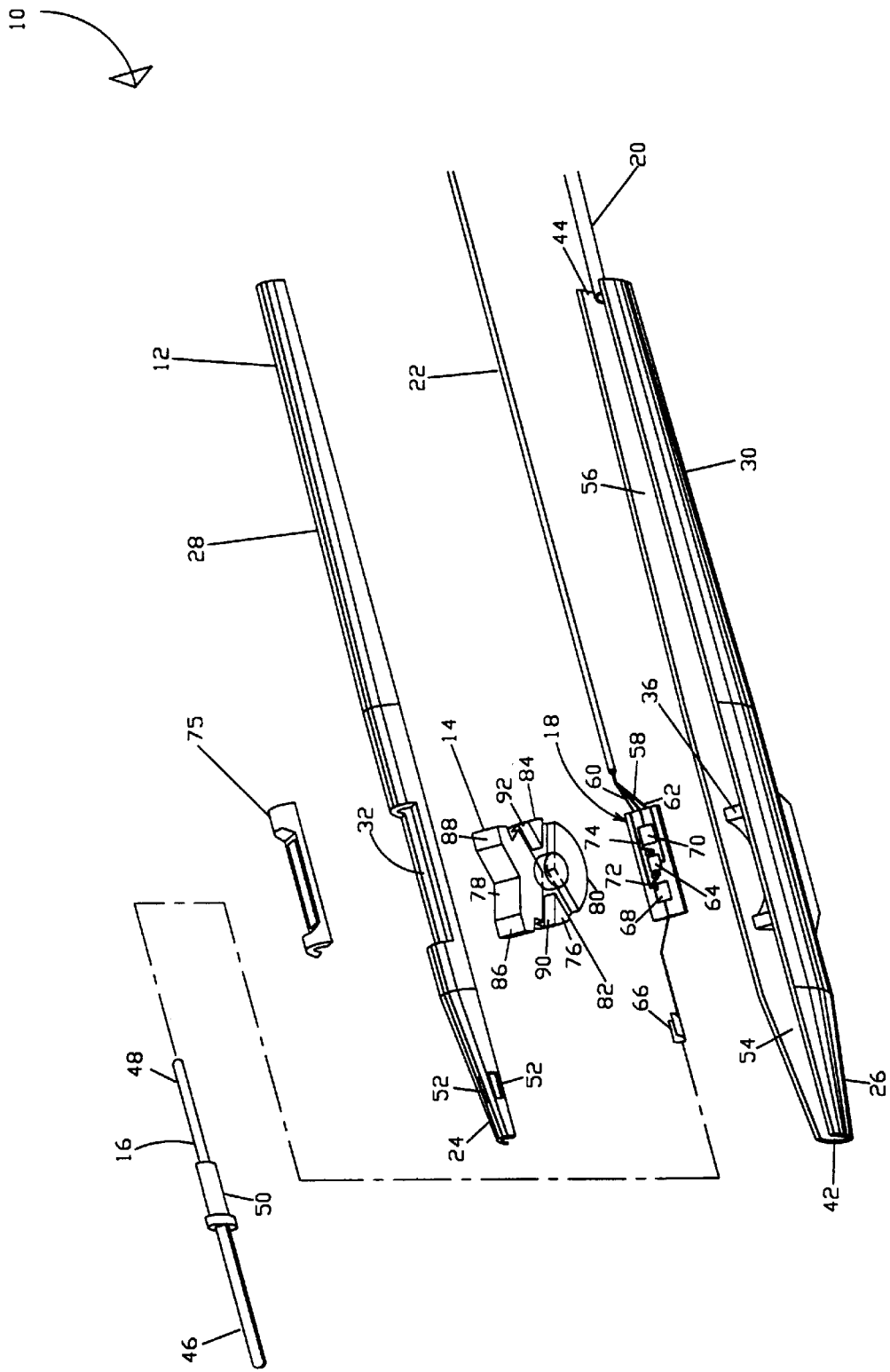
FIG. 1 is an exploded view of the self-evacuating electrocautery device according to the present invention illustrating the device having a hollow body with an upper body portion and a lower body portion and an electrical and intermittent self-centering switch mechanism.

As illustrated in FIG. 1, the present invention is a disposable self-evacuating electrocautery device, indicated generally at 10, for removing plume created by searing and coagulating tissue and the like during surgical operations with the electrocautery device 10. Typically, the electrocautery device 10 of the present invention comprises an elongated hollow body 12, an intermittent self-centering rocker switch 14, a disposable electrocautery blade 16, an electrical contact member 18, flexible plume vacuum tubing 20 connected to a vacuum system (not shown) and an insulated electrical cable 22 electrically connected to a conventional electrosurgical generator (not shown). While the electrocautery device 10 is preferably prepackaged in sterilized containers to be used once and then disposed, it is within the scope of the present invention to have the electrocautery device 10 be non-disposable and disinfectable for re-use by known procedures in the art.

Figure 2:
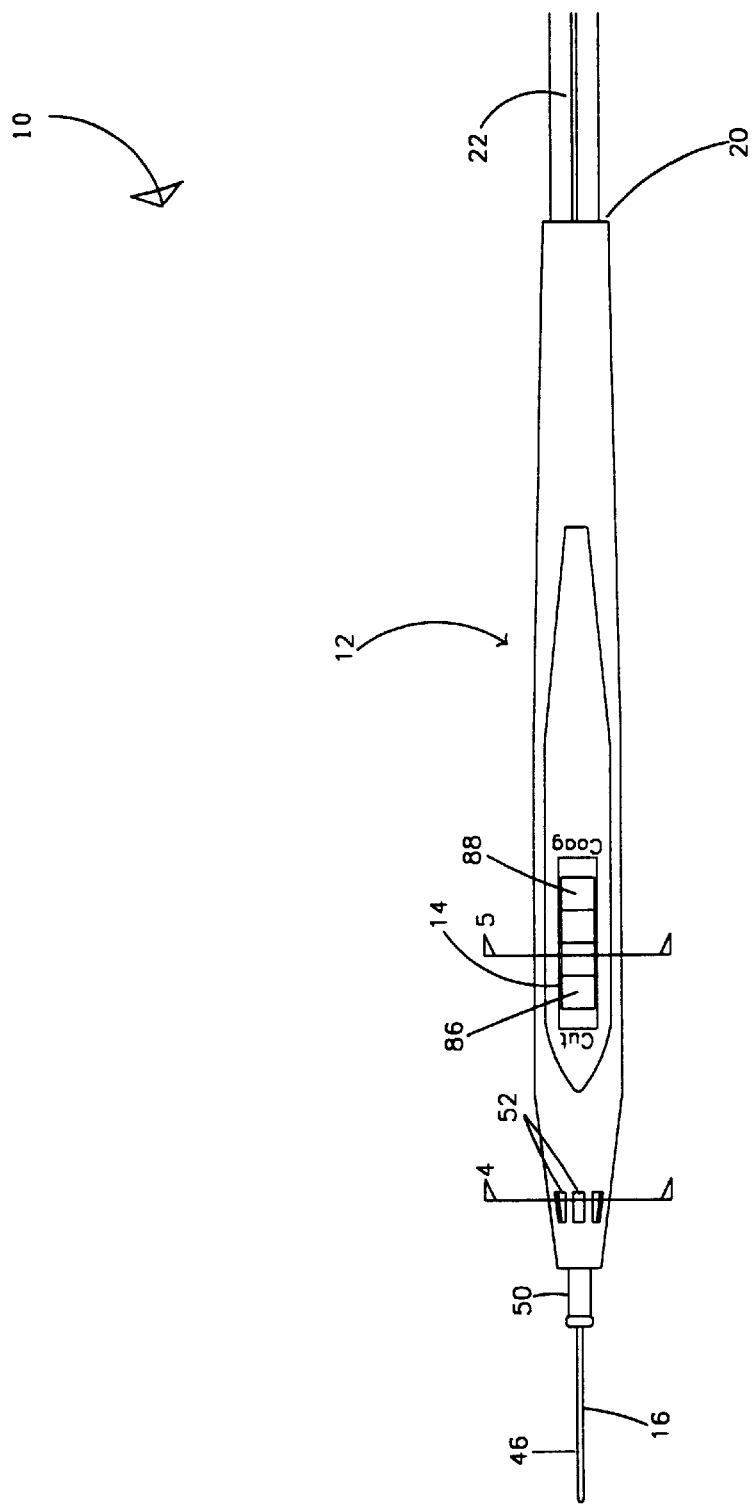
FIG. 2 is a top view of the self-evacuating electrocautery device according to the present invention.
Figure 3:
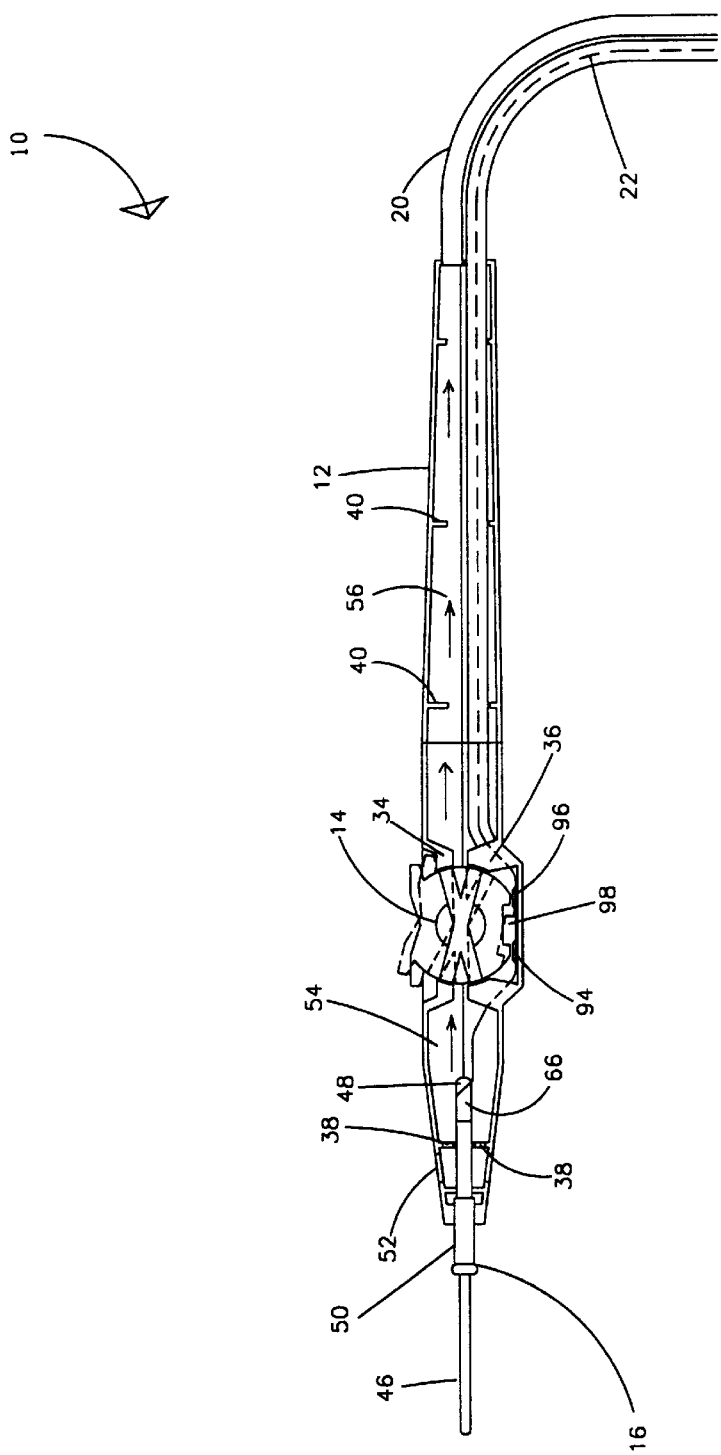
FIG. 3 is a side sectional view of the self-evacuating electrocautery device according to the present invention illustrating the device having a hollow body having an opening therein, switch means positioned within the opening and conducting surfaces positioned within the hollow body for use in plume evacuation.

Still referring to FIG. 1 and now also to FIG. 2, the hollow body 12 of the electrocautery device 10 has a first end 24 and a second end 26 and comprises a first body portion 28 and a second body portion 30. The first body portion 28 includes a switch receiving opening 32 for receiving the switch 14 and, as illustrated in FIG. 3, integral first switch stabilizing supports 34 within the switch opening 32. Referring back to FIG. 1, the second body portion 30 includes integral second switch stabilizing supports 36 cooperating with the first switch stabilizing supports 34 of the first body portion 28 to inhibit lateral movement of the switch 14 within the hollow body 12. Preferably, the first body portion 28 is fixably secured to the second body portion 30 by ultrasonic welding or other means including, but not limited to, adhesive, mechanical means, etc.

As illustrated in FIG. 3, the first body and second body portions 28, 30 of the hollow body 12 further include a plurality of first spaced ribs 38 integrally adjacent the first end 24 of the hollow body 12 and a plurality of second spaced ribs 40 along and integrally adjacent the second end 26 of the hollow body 12 on both the first body portion 28 and the second body portion 30. The first and second ribs 38, 40, along with the first and second switch stabilizing supports 34, 36, are preferably formed integral to the first and second body portions 28, 30, respectively, from the same materials used to form the hollow body 12 during construction of the hollow body 12. While described as being integral to the first and second body portions 28, 30, it is within the scope of the present invention, however, to construct the first and second ribs 38, 40, and the first and second switch stabilizing supports 34, 36, from a different material than the material used for the hollow body 12 and, also, to add the first and second ribs 38, 40 and the first and second switch stabilizing supports 34, 36 to the first and second body portions 28, 30, respectively, after the hollow body 12 has been constructed.

The hollow body 12, in a preferred embodiment of the electrocautery device 10 of the present invention, is constructed from an inexpensive, thermoplastic, electrically non-conductive material. It is within the scope of the present invention, however, to construct the hollow body 12 from other materials including, but not limited to, ceramic, wood, other plastics, etc.

The hollow body 12 of the electrocautery device 10 additionally comprises a first opening 42 formed in the first end 24 of the hollow body 12 for receiving the blade 16 and a second opening 44 formed in the second end 26 of the hollow body 12 opposite the first opening 42 for receiving the cable 22 and the plume vacuum tubing 20 as best illustrated in FIG. 1. The blade 16 of the electrocautery device 10 comprises a blade portion 46 for use in alternatively searing or coagulating tissue and the like during surgery, a contact end 48 opposite the blade portion 46 for contacting the electrical contact member 18, and an insulating sheath 50 positioned about the blade substantially between the blade portion 46 and the contact end 48. The blade 16 is positioned such that the insulating sheath 50 of the blade 16 is seated and secured within the first end 24 of the hollow body 12 between the first body portion 28 and the second body portion 30 with the blade portion 46 extending away from the hollow body 12. The first spaced ribs 38 of the hollow body 12 inhibits lateral and transverse movement of the blade 16 within the hollow body 12.

Figure 4:
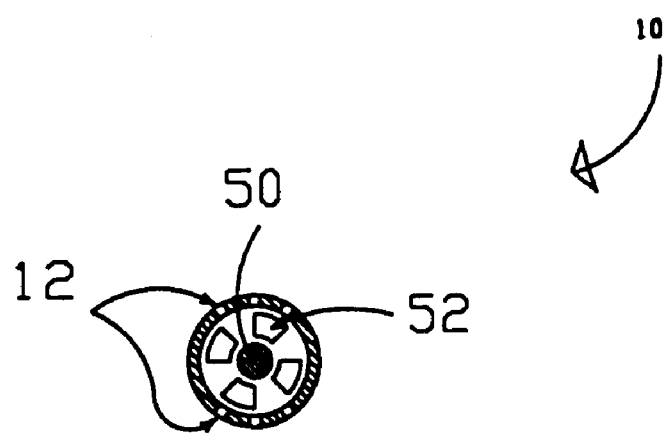
FIG. 4 is a front sectional view of the self-evacuating electrocautery device according to the present invention taken along line 4 in FIG. 2 and illustrating the body having a plurality of plume intake ports and a plurality of airway openings.

As best illustrated in FIGS. 2 and 4, the hollow body 12 also comprises a plurality of plume intake ports 52 feeding, as illustrated in FIG. 3, into a first airway path 54 at the first end 24 of the hollow body 12 and defined by the first and second body portions 28, 30 of the hollow body 12. The plume intake ports 52 are positioned about the first end 24 of the hollow body 12 in close proximity to the blade 12 to effectively remove the plume created during surgical operations. In an embodiment illustrated in FIG. 4, the plume intake ports 52 are in a circumferential configuration about the first end 24 of the hollow body 12. Now referring back to FIG. 3, a second airway path 56 is defined by the first and second body portions 28, 30 at the second end 26 of the hollow body 12 and cooperates with the vacuum tubing 20 to remove the plume from the hollow body 12. Function and operation of the plume intake ports 52 in conjunction with the first and second airway paths 54, 56 and the plume vacuum tubing 20 will be described in further detail below.

As illustrated in FIG. 1, the electrical cable 22 of the electrocautery device 10 includes a main insulated contact wire 58, an insulated searing switch wire 60, and an insulated coagulating switch wire 62. The electrical cable 22 is positioned within the second airway path 56 in the second end 26 of the hollow body 12 and extends rearwardly away from the hollow body 12 through the second opening 44 in the second end 26 of the hollow body 12 to a conventional plug (not shown) attached to the electrosurgical generator. The electrosurgical generator provides electrical energy to the electrical cable 22 and to the vacuum system to remove plume from the area about the blade 16 and the hollow body 12 as will be described in further detail below.

As mentioned briefly above, the electrocautery device 10 of the present invention comprises a contact member 18 seated within the second switch stabilizing supports 36 of the second body portion 30 of the hollow body 12. The contact member 18 comprises a main conducting strip 64 electrically connected to the contact end 48 of the blade 16 via a blade receiver 66. The blade receiver 66 resiliently receives the blade 16 and is electrically connected to the main contact wire 58 on the electrical cable 22 to provide electrical connection between the main contact wire 58 and the blade 16.

Still referring to FIG. 1, the contact member 18 further comprises a searing switch conducting strip 68 and a coagulating switch conducting strip 70 mounted adjacent to and selectively connectable to the main conducting switch 64. The main conducting strip 64 includes an electrically connected, slightly elevated searing raised member 72 and an electrically connected, slightly elevated coagulating raised member 74. The searing and coagulating raised members 72, 74 are movable into contact with the searing and coagulating conducting strips 68, 70, respectively, and serve as electrical contacts for the switch 14 upon rotation of the switch 14 into searing and coagulating positions, respectively, to sear and coagulate tissue as desired.

The electrical contact member 18 is preferably formed from a single metal stamping. It should be noted, however, that construction of the contact member 18 by other means, besides metal stamping, is within the scope of the present invention.

The switch 18 of the electrocautery device 10 of the present invention, as illustrated in FIG. 1 and FIG. 3, is positioned within the switch receiving opening 32 in the first body portion 28 of the hollow body 12 and seated on the second switch stabilizing supports 36 on the second body portion 30 of the hollow body 12. As illustrated in FIG. 1, a switch cover plate 75 is, preferably, mounted over the switch 18 and the switch receiving opening 32 to inhibit foreign material from entering or escaping the hollow body 12 from around the switch 18.

As illustrated in FIG. 3, the switch 18, when not in use, self-centers into a neutral, non-electrical contact position. On the other hand, the switch 18, in operation, is intermittently movable into either a searing position, as illustrated in phantom in FIG. 3, or a coagulating position and controls the electrical current delivered to the blade 16 while correspondingly activating the vacuum system and the self-evacuating features of the electrocautery device 10 of the present invention. Both the electrical control by the switch 14 and the self-evacuating features of the electrocautery device 10 of the present invention will be discussed in more detail below.

The switch 14 of the electrocautery device 10 of the present invention, as illustrated in FIG. 1, includes a switch body 76 having top surface 78, a bottom surface 80 opposite the top surface 78, and a first and second rounded side surfaces 82, 84 between the top surface 78 and the bottom surface 80. The first and second rounded side surfaces 82, 84 allow the switch 14 to rotatably move within the first and second stabilizing supports 34, 36 of the hollow body 12 of the electrocautery device 10 into and out of the searing and coagulating positions.

Figure 5:
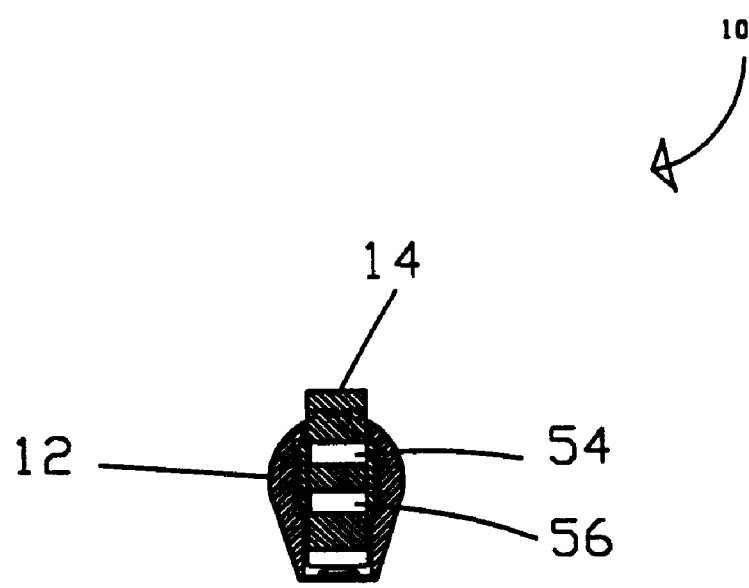
FIG. 5 is a sectional view of the self-evacuating electrocautery device according to the present invention taken along line FIG. 5 in FIG. 2 and illustrating the intermittent self-centering switch mechanism.

The switch body 76 further includes a searing activation surface 86 positioned on the top surface 78 of the switch body 76 for moving the switch 14 into the searing position, a coagulating activation surface 88 positioned on the top surface 78 of the switch body 76 spaced from the searing activation surface 86 for moving the switch 14 into the coagulating position, and first and second intersecting plume airway paths 90, 92, also illustrated in FIG. 5, connecting through the first and second side rounded surfaces 82, 84 and the switch body 76. The first and second intersecting plume airway paths 90, 92 provide a path for the plume created during surgical operations such that the plume can travel through the plume intake ports 52, through the first airway path 54 of the first end 24 of the hollow body 12, through either of the first or second plume airway paths 90, 92 depending on the position of the switch 14, through the second airway path 56 of the second end 26 of the hollow body 12, and into the vacuum tubing 20. The vacuum tubing 20 is connected to a conventional waste receptacle (not shown) for collecting the plume and the like for disposal in accordance with federal, state, and local regulations.

As illustrated in FIG. 3, the switch body 76 further includes a searing protuberance 94 on the bottom surface 80 of the switch body 76 substantially opposite the searing activation surface 86 and contact ably adjacent the searing switch conducting strip 68 of the contact member 18. Also, the switch body 76 includes a coagulating protuberance 96 on the bottom surface 80 of the switch body 76 and substantially opposite the coagulating activation surface 88 and contact ably adjacent the coagulating switch conducting strip 70 of the contact member 18. A recessed area 98 is formed the bottom surface 80 of the switch body 76 between the searing and coagulating protuberances 94, 96 to better define the searing and coagulating protuberance 94, 96 assuring contact between the searing protuberance 94 and the searing switch conducting strip 68 and between the coagulating protuberance 96 and the coagulating switch conducting strip 70.

The procedure of using the electrocautery device 10 of the present invention will now be described. In use, a surgeon or other medical professional grasps the electrocautery device 10 and positions the electrocautery device 10 adjacent the desired tissue to be seared or coagulated. To sear the desired tissue, the surgeon or other medical professional activates the electrocautery device 10 into the searing position by applying pressure to the searing activation surface 86 on the switch body 76 of the switch 14. The pressure on the searing activation surface 86 causes the searing protuberance 94 to move into contact with the searing raised member 72 and causes the searing raised member 72 to contact the searing switch conducting strip 68. The contact between the searing raised member 72 and the searing switch conducting strip 68 connects the circuit between the searing switch conducting strip 68 and the main conducting switch 64 to provide both electrical energy to the blade 16 to sear the desired tissue and electrical energy to the vacuum to evacuate the plume associated with the searing of the desired tissue.

When the searing protuberance 94 on the switch body 76 causes the searing raised member 72 to contact searing switch conducting strip 68, the first plume airway path 90 in the switch body 76 of the switch 14 aligns with the first and second airway paths 54, 56 in the hollow body 12 thereby connecting the plume intake ports 52 with the vacuum tubing 20 and, thus, the waste receptacle. The second plume airway path 92 is effectively closed by the first and second stabilizing supports 36, 38 on the first and second body portions 28, 30, respectively. When the desired searing is completed, the surgeon or other medical professional releases the pressure on the searing activation surface 86 of the switch body 76 causing the switch body 76 to rotate back to the neutral position moving the searing protuberance 94 out of contact with the searing raised member 72 thereby disconnecting the connection and circuit between the searing raised member 72 and the searing switch conducting strip 68 ceasing electrical current to both the blade 16 and the vacuum.

Coagulation of tissue utilizing the electrocautery device 10 of the present invention is similar to the procedures for searing tissue. To coagulate tissue and the like, the surgeon or other medical professional activates the electrocautery device 10 into the coagulating position by applying pressure to the coagulating activation surface 88 on the switch body 76 of the switch 14. The pressure on the coagulating activation surface 88 causes the coagulating protuberance 96 to move into contact with the coagulating raised member 74 and causes the coagulating raised member 74 to move into contact with the coagulating switch conducting strip 80. The contact between the coagulating raised member 74 and the coagulating switch conducting strip 80 connects the circuit between the coagulating switch conducting strip 80 and the main conducting switch 64 to provide electrical current to the blade 16 to coagulate the desired tissue and activate the vacuum on the waste receptacle.

When the coagulating protuberance 96 on the switch body 76 moves into contact with the coagulating switch conducting strip 70, the second plume airway path 92 in the switch body 76 aligns with the first and second airway paths 54, 56 in the hollow body 12 thereby connecting the plume intake ports 52 with the vacuum tubing 20 and the waste receptacle. The first plume airway path 90 is effectively closed by the first and second stabilizing supports 34, 36 on the first and second body portions 28, 30, respectively. When the desired coagulating is completed, the surgeon or other medical professional releases the pressure on the coagulating activation surface 88 of the switch body 76 causing the switch body 76 to rotate back to the neutral position moving the coagulating protuberance 96 out of contact with the coagulating raised member 74 thereby disconnecting the connection and circuit between the coagulating raised member 74 and the coagulating switch conducting strip 70 ceasing electrical current to both the blade 16 and the vacuum.

It thus follows that when the electrocautery device 10 of the present invention is in use, being connected to both the electrosurgical generator and the vacuum source, the mutagenic plume created by contact of the blade 16 with the tissue will be immediately evacuated from the operating site to the vacuum source. Of course, suitable filtering systems may be associated with the vacuum system to dispose of contaminants in the materials being drawn to the vacuum source.

From the foregoing, it will be appreciated that an electrocautery device 10 constructed according to the present invention provides a means whereby a plume generated during the electrocauterization process may be evacuated from the area as soon as it is generated. It should be particularly noted that the increased noise levels associated with full time vacuum use will be significantly lower due to the intermittent nature of the vacuum associated with the present invention, thus facilitating communication between the medical staff in the operating environment.

The foregoing exemplary descriptions and the illustrative preferred embodiments of the present invention have been explained in the drawings and described in detail, with varying modifications and alternative embodiments being taught. While the invention has been so shown, described and illustrated, it should be understood by those skilled in the art that equivalent changes in form and detail may be made therein without departing from the true spirit and scope of the invention, and that the scope of the present invention is to be limited only to the claims except as precluded by the prior art. Moreover, the invention as disclosed herein, may be suitably practiced in the absence of the specific elements which are disclosed herein.

We claim:

1. An electrocautery device for selectively providing electrical energy from an electrosurgical generator for alternatively searing and coagulating tissue of a patient during surgery, the electrocautery device having a blade and an electrical cable, the cable for electrically connecting the blade to the electrosurgical generator, the device comprising:

a main body having an elongated hollow body, a first opening, and a second opening, the first opening receiving the blade and the second opening receiving the electrical cable;

vacuum means formed in the main body for selectively providing a vacuum for removing any plume created while searing or coagulating tissue with the blade of the electrocautery device wherein the vacuum means comprises at least one intake port formed adjacent the first opening of the hollow body, a vacuum tubing extending through the second opening of the hollow body and connected to the intake port; and switch means secured to the main body for selectively controlling the electrical energy to the blade, the switch means having a self-centering switch body rotatable within the hollow body to selectively activate the electrical energy of the electrosurgical generator to either sear or coagulate tissue and to activate the vacuum means upon activation of the electrical energy and further comprises path means formed in the switch body for selectively connecting the intake port to the vacuum tubing upon activation of both the electrical energy to either sear or coagulate tissue, the path means having a pair of intersecting airway paths alternatingly alignable within the hollow body to connect the intake port to the vacuum tubing upon activation of both the electrical energy and the vacuum means.

2. The device as claimed in claim 1 and further comprising an electrical contact within the main body, the electrical contact electrically connecting the blade and the electrical cable to selectively control the electrical charge to the blade to either sear or coagulate tissue and to activate the vacuum means.

3. The device as claimed in claim 2 wherein the electrical contact comprises means for releasably securing the blade to the electrical contact.

4. The device as claimed in claim 11 wherein the hollow body comprises a first body portion and a second body portion, the first body portion being secured to the second body portion.

5. The device as claimed in claim 4 wherein the first body portion is secured to the second body portion by ultrasonic welding.

6. The device as claimed in claim 4 wherein the first and second body portions include a plurality of ribs adjacent the first and second openings of the hollow body to inhibit movement of the blade and electrical cable, respectively, within the hollow body.

7. The device as claimed in claim 4 wherein the first and second body portions include stabilizing supports about the switch means to inhibit movement of the switch means along the longitudinal length of the hollow body.

8. An electrosurgical instrument for selectively providing electrical energy from an electrosurgical generator to a patient for searing and coagulation, the electrosurgical instrument having an electrode blade, the instrument comprising:

a hollow elongated body having a first hollow portion and a second hollow portion;

a cable adapted to be connected to the electrosurgical generator, the cable including a main insulated contact wire, and first and second insulated switch wires;

a main conducting strip positioned within the elongated body and connected electrically to the electrode blade;

a first switch conducting strip and a second switch conducting strip, the first and second switch conducting strips selectively connectable to the main conducting strip;

a blade receiver within the elongated body resiliently receiving the electrode blade and electrically connected to the main contact wire to provide electrical connection between the main contact wire and the electrode blade, the electrode blade extending from the first hollow portion of the elongated body;

at least one plume intake port formed in the elongated body adjacent the electrode blade for receiving the plume associated with the searing and coagulation of tissue into the first hollow portion of the elongated body;

switch means between the first and second hollow portions of the elongated body for selectively connecting one of the first and second switch conducting strips to the main conducting strip such that a selected electrical energy is transmitted along the main conducting strip to the electrode blade and from the generator via the main contact wire;

airway path means within the switch means connecting the first hollow portion to the second hollow portion and allowing the plume to travel from the first hollow portion to the second hollow portion when the switch means selectively connects one of the first and second switch conducting strips to the main conducting strip; and vacuum means connected to the second hollow portion to evacuate the plume from the second hollow portion, the vacuum means activated upon the switch means selectively connecting one of the first and second switch conducting strips to the main conducting strip;

wherein the airway path means comprise a first airway and a second airway the first and second airways intersecting within the switch means, the first and second airways alternatingly connecting the first and second hollow portions when the switch means selectively connects one of the first and second switch conducting strips to the main conducting strip.

9. The electrosurgical instrument as claimed in claim 8 wherein the elongated body includes a plurality of ribs about the electrode blade to inhibit movement of the electrode blade about the first hollow portion.

10. The electrosurgical instrument as claimed in claim 8 wherein the elongated body includes a first portion and a second portion, the first portion being secured to the second portion by ultrasonic welding.

11. The electrosurgical instrument as claimed in claim 8 wherein the first switch conducting strip includes a first raised member and the second switch conducting strip includes a second raised member, the first and second raised members serving as electrical contacts for the switch means.

12. The electrosurgical instrument as claimed in claim 11 wherein the switch means comprises an upper surface and a lower surface, a searing surface and a coagulation surface on the upper surface, and a searing protrusion and a coagulation protrusion on the lower surface such that (a) downward pressure on the searing surface moves the searing protrusion into contact with the first raised member and the first raised member into contact with the first conducting strip, and (b) downward pressure on the coagulation surface moves the coagulation protrusion into contact with the second raised member and the second raised member into contact with the second conducting strip.

13. The electrosurgical instrument as claimed in claim 8 wherein the first and second airways intersect approximate a mid-portion of the switch means.

14. The electrosurgical instrument as claimed in claim 8 wherein upon alignment of the first airway with the first and second hollow portions, the second airway is effectively blocked to the passage of plume therethrough and wherein upon alignment of the second airway with the first and second hollow portions, the first airway is effectively blocked to the passage of plume therethrough.

* * * * *